United States Patent
Rouet et al.

(10) Patent No.: US 10,499,864 B2
(45) Date of Patent: Dec. 10, 2019

(54) CONTRAST ARRIVAL DETECTION

(71) Applicant: KONINKLIJKE PHILIPS N.V., Eindhoven (NL)

(72) Inventors: Laurence Rouet, Paris (FR); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 210 days.

(21) Appl. No.: 15/510,710

(22) PCT Filed: Sep. 15, 2015

(86) PCT No.: PCT/EP2015/071081
§ 371 (c)(1),
(2) Date: Mar. 13, 2017

(87) PCT Pub. No.: WO2016/046024
PCT Pub. Date: Mar. 31, 2016

(65) Prior Publication Data
US 2017/0281106 A1    Oct. 5, 2017

(30) Foreign Application Priority Data
Sep. 22, 2014 (EP) .................................... 14306450

(51) Int. Cl.
*A61B 6/00* (2006.01)
*A61B 6/12* (2006.01)

(52) U.S. Cl.
CPC .............. *A61B 6/481* (2013.01); *A61B 6/12* (2013.01); *A61B 6/486* (2013.01); *A61B 6/487* (2013.01);
(Continued)

(58) Field of Classification Search
CPC ........... A61B 6/481; A61B 6/12; A61B 6/486; A61B 6/487; A61B 6/507
See application file for complete search history.

(56) References Cited

U.S. PATENT DOCUMENTS 8,655,041 B2    2/2014  John
2012/0128226 A1  5/2012  John
(Continued)

FOREIGN PATENT DOCUMENTS

EP    2662830 A1    11/2013
JP    2010022667 A   2/2010
(Continued)

OTHER PUBLICATIONS

Chen, Terrence et al "Robust and Fast Contrast Inflow Detection for 2D X-ray Fluoroscopy", MICCAI 2011, Part 1, LNCS 6891, pp. 243-250, 2011.

*Primary Examiner* — Joseph M Dietrich

(57) ABSTRACT

The present invention relates to detection of contrast agent arrival in X-ray imaging. In order to provide an improved way of detecting contrast agent arrival in X-ray imaging for reducing the delay in the detection, a temporal sequence of X-ray image data is provided (102) comprising a plurality of frames with a field of view of an anatomy of interest and an inserted catheter for delivery of contrast agent, wherein, in the field of view, contrast agent is injected with the catheter during the temporal sequence. At least one location for measuring contrast in each of the frames is determined (104), wherein the at least one location for measuring contrast pertains to a portion of the catheter in the field of view in the image data. Contrast is measured (106) at the at least one location for each of the frames at least in the image part pertaining to the portion of the catheter. A change of the measured contrast along time at the at least one location pertaining to the portion of the catheter is determined (108). Further, an instant of contrast agent arrival in the field of view of the anatomy of interest is provided (110) as a function of the instant along time with the change of contrast.

14 Claims, 5 Drawing Sheets

(52) U.S. Cl.
CPC ............ *A61B 6/507* (2013.01); *A61B 6/5205* (2013.01); *A61B 6/5217* (2013.01)

(56) References Cited

U.S. PATENT DOCUMENTS

2012/0134553 A1   5/2012   Liao
2012/0300903 A1   11/2012  Yao
2013/0345559 A1   12/2013  Haemmerich

FOREIGN PATENT DOCUMENTS

WO   2008104909 A1   9/2008
WO   2010044001 A2   4/2010
WO   2010150145 A1   12/2010

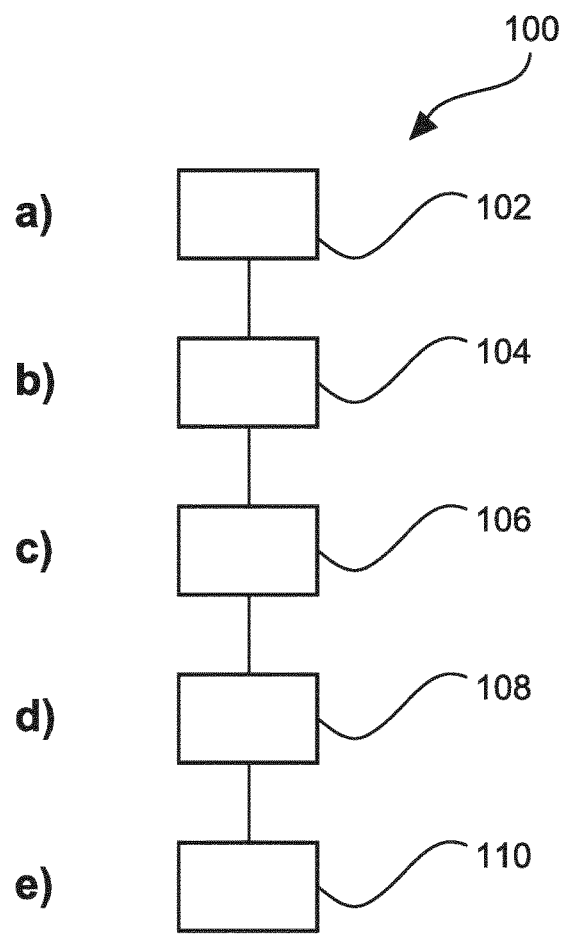
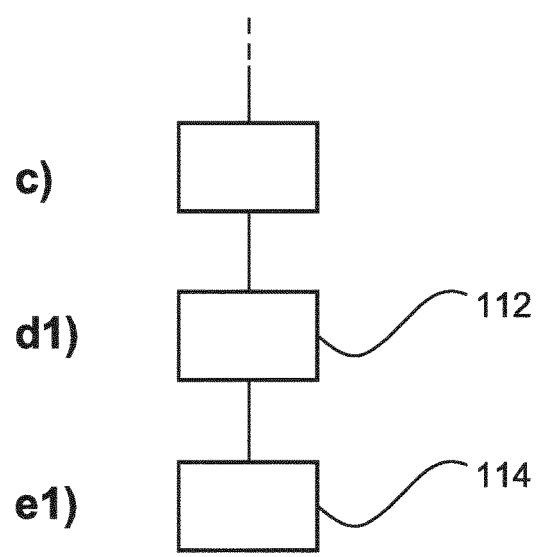

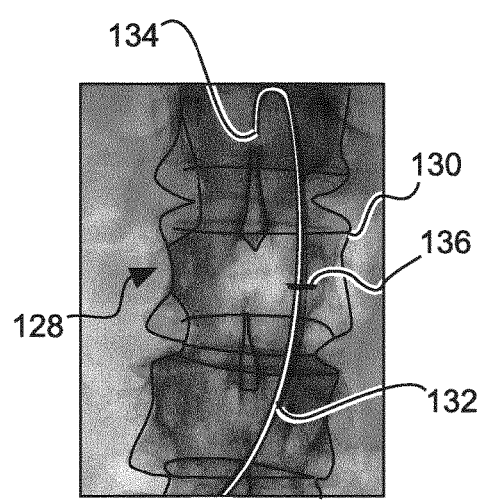 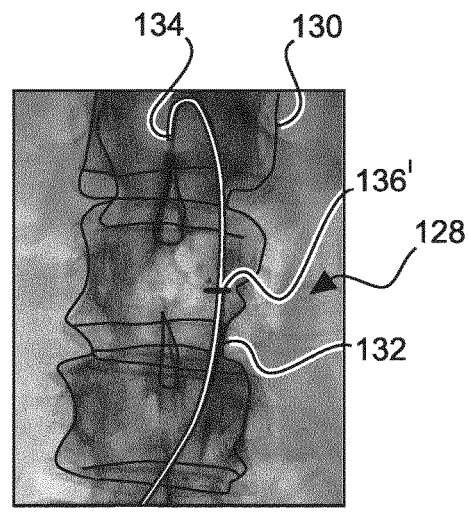
Fig. 9a  Fig. 9b
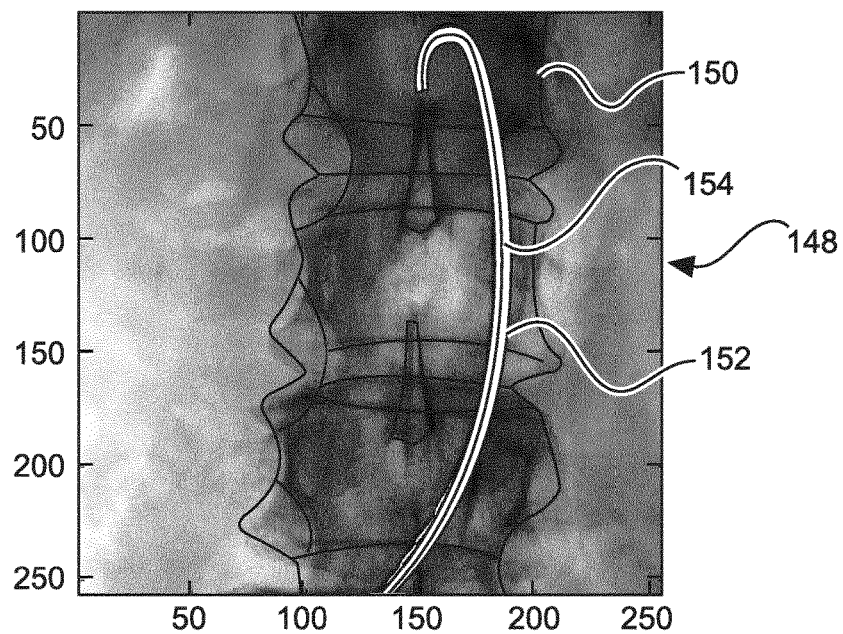
Fig. 10

CONTRAST ARRIVAL DETECTION

CROSS-REFERENCE TO PRIOR APPLICATIONS

This application is the U.S. National Phase application under 35 U.S.C. § 371 of International Application No. PCT/EP2015/071081, filed on Sep. 15, 2015, which claims the benefit of European Patent Application No. 14306450.9, filed on Sep. 22, 2014. These applications are hereby incorporated by reference herein.

FIELD OF THE INVENTION

The present invention relates to detection of contrast agent arrival in X-ray imaging, and relates in particular to an image processing device, to a system for interventional medical X-ray imaging, to a method for detection of contrast agent arrival in X-ray imaging, to a computer program element and to a computer-readable medium.

BACKGROUND OF THE INVENTION

In interventional X-ray imaging, the detection of the instant when contrast agent arrives in the field of view is used for different applications. For example, in digital subtraction angiography (DSA), mask images may be selected prior to contrast injection. The detection of the instant when injection of contrast agent takes place has been shown to optimize the masking process. For example, EP 2 662 830 A1 relates to DSA and describes an evaluation step of calculating evaluation values indicating the states of the injection of the radiopaque dye for each of the frames constituting the DSA images. US 2012/0128226 A1 relates to automatic detection of contrast injection and describes the measure of image intensity to be determined for each of the subtracted images. In WO 2010/044001 A2, for visualizing an object of interest together with a device, a combined device and anatomy boosting is described. Since the device is already visible in X-ray imaging, the instant when contrast agent reaches the device, the contrast agent is used to visualize the anatomy. The arrival of the contrast agent is monitored in the vicinity of the device. WO 2008/104909 relates to recording a vascular structure during an intervention. An injection of a contrast agent provided to the vicinity of a device landmark is detected and the vicinity of the device landmark is monitored. Time contrast curves based on the monitored vicinity of the device landmark are generated and analyzed to determine a best instant as a visibility optimum based on the time contrast curves. The arrival of the contrast agent is looked for and analyzed in an area besides the device landmark.

However, it has been shown that this is not always easily possible and may also imply some delays, for example the first injected frames might only be weakly injected and hence the contrast arrival may be detected with a delay. It has been shown further that in certain interventions, real time minimally delayed injection detection is required.

SUMMARY OF THE INVENTION

There may thus be a need to provide an improved way of detecting contrast agent arrival in X-ray imaging for reducing the delay in the detection.

The object of the present invention is solved by the subject-matter of the independent claims, wherein further embodiments are incorporated in the dependent claims. It should be noted that the following described aspects of the invention apply also for the image processing device, for the system for interventional medical X-ray imaging, and for the method for detection of contrast agent arrival in X-ray imaging, as well as for the computer program element and the computer-readable medium.

According to the present invention, a method for detection of contrast agent arrival in X-ray imaging is provided. The method comprises the following steps:

a) providing a temporal sequence of X-ray image data comprising a plurality of frames with a field of view of an anatomy of interest and an inserted catheter for delivery of contrast agent; in the field of view, contrast agent is injected with the catheter during the temporal sequence;

b) determining at least one location for measuring contrast in each of the frames, wherein the at least one location for measuring contrast pertains to a portion of the catheter along a length of the catheter in the field of view in the image data;

c) measuring contrast at the at least one location for each of the frames at least in the image part pertaining to the portion of the catheter;

d) determining a change of the measured contrast along time at the at least one location pertaining to the portion of the catheter; and e) providing an instant of contrast agent arrival in the field of view of the anatomy of interest as a function of the instant along time with the change of contrast.

The change relates to a change of contrast indicating the increased presence of contrast agent. For example, the change may be a maximum change of the measured contrast, an average change of the measured contrast, a substantial change of the measured contrast, or any other changes that can indicate the increased presence of contrast agent.

As an advantage, by measuring the contrast arrival on the catheter, i.e. on the image data relating to the catheter, an early detection is ensured and a delay of contrast agent arrival is thus minimized. The contrast is hence determined not in a portion of the image that relates to an anatomy that is injected with the contrast agent, for example a vessel, but relates to the contrast agent arriving in the catheter itself, before it arrives in the anatomy.

The instant of arrival of the contrast agent may derive from the instant of contrast change (e.g. maximum contrast change or substantial change) in the particular location. However, this may also be equal, but it may also be not equal and there is provided an additional offset (or shift) of the instant of contrast change in order to account, for example, for a remaining catheter length that the contrast agent has to travel through before reaching a targeted anatomy area.

The term "instant along time" relates to "an instant in time". For example, the instant refers to a (temporal, i.e. time-wise) frame-index. The term "instant along time" is also referred to as "instant".

In an example, this function is provided as a fixed, i.e. predetermined (temporal) offset. In another example, this function is provided as an identity of the instant corresponding to the measured contrast along time.

According to an example, in step e) for providing the instant of contrast agent arrival, the instant along time with the change of the contrast is provided as an indicator of a starting, i.e. starting instant, of contrast injection of the anatomy of interest.

In an example, in step e) for providing the instant of contrast agent arrival, the instant along time with the maximum change of the contrast is provided as an indicator of a starting, i.e. starting instant, of contrast injection of the anatomy of interest.

Besides maximum contrast change, the contrast change may also be a substantial change or an average change of the measured contrast.

According to an example, the change of the contrast comprises a maximum change of the measured contrast.

In an example, in step d), a maximum change of the measured contrast along time is determined at the at least one location pertaining to the portion of the catheter. In step e), an instant of contrast agent arrival is provided in the field of view of the anatomy of interest as a function of the instant along time with the maximum change of contrast.

According to an example, in step c), the contrast is measured as a contrast of a location on the catheter with respect to a surrounding of the catheter.

In an example, the term measuring contrast also relates to measuring a grey value, or intensity value for a location along time.

In an example, it is provided that the anatomy and the catheter are arranged in such a way that no, or only minimal relative motion occurs. Hence, the surrounding can be omitted, because it is so-to-speak constant. The surrounding will not modify the finding. The measurement can be restricted to the catheter location. In other words, in the example, the measurement is a grey-level average that will be monitored over time.

According to an example, the at least one location for measuring contrast is registered with the catheter such that when the catheter moves in relation with the image frame of reference, also the at least one location for measuring contrast moves in the image in relation to the image frame of reference.

For example, the catheter can be moved by clinical staff, e.g. a surgeon, e.g. the catheter may be pushed or pulled in the anatomy.

In an example, the at least one location for measuring contrast is registered with the catheter such that when the catheter moves in relation with the anatomy shown in the image data, also the at least one location for measuring contrast moves in the image in relation to the anatomy.

According to an example, in step c), for measuring the contrast, contrast profiles are extracted and, preferably, the contrast profiles are extracted for a profile length that covers at least the width of the catheter and that is oriented in a profile direction transverse to a main catheter direction.

By providing and comparing contrast profiles over the width of the catheter, it is ensured that even an uneven distribution of contrast inside the catheter in the beginning of the contrast injection phase is detected.

According to an example, in step c), contrast profiles are extracted for a number of locations over a length of the catheter. Following step c), integrals of the contrast profiles are provided and in step d), the integrals are compared.

According to an example, for the determining in step b), the catheter is extracted. Preferably, in step b), for the extraction of the catheter in the frame it is provided to extract at least one of the group of centreline of the catheter in the frame, outline of the catheter in the frame, and projected area of the catheter in the frame.

However, extraction of the full catheter is not mandatory. In one example, only the identification of a location pertaining to the catheter is required. This can for instance be the tip of the catheter, which can be identified by a tip detector and tracker. Likewise, a sharp angle in the catheter is a well identifiable location, which can be detected and tracked through traditional second-derivative or curvature feature extractors.

According to the present invention, also an image processing device for detection of contrast agent arrival in X-ray imaging is provided. The image processing device comprises an input unit, a processing unit and an output unit. The input unit is configured to provide image data comprising a plurality of frames with a field of view of an anatomy of interest and an inserted catheter for delivery of contrast agent. In the field of view, contrast agent is injected with the catheter during the temporal sequence. The processing unit is configured to determine at least one location for measuring contrast in each of the frames, wherein the at least one location for measuring contrast pertains to a portion of the catheter along a length of the catheter in the field of view in the image data. The processing unit is further configured to measure contrast agent at the at least one location for each of the frames at least in the image part pertaining to the portion of the catheter. The processing unit is further configured to determine a change of the measured contrast along time at the at least one location pertaining to the portion of the catheter. The output unit is configured to provide an instant of contrast agent arrival in the field of view of the anatomy of interest as a function of the instant along time with the change of contrast.

According to an example, the change of the contrast comprises a maximum change of the measured contrast.

In an example, an image processing device for detection of contrast agent arrival in X-ray imaging is provided. The image processing device comprises an input unit, a processing unit and an output unit. The input unit is configured to provide image data comprising a plurality of frames with a field of view of an anatomy of interest and an inserted catheter for delivery of contrast agent. In the field of view, contrast agent is injected with the catheter during the temporal sequence. The processing unit is configured to determine at least one location for measuring contrast in each of the frames, wherein the at least one location for measuring contrast pertains to a portion of the catheter in the field of view in the image data. The processing unit is further configured to measure contrast agent at the at least one location for each of the frames at least in the image part pertaining to the portion of the catheter. The processing unit is further configured to determine a maximum change of the measured contrast along time at the at least one location pertaining to the portion of the catheter. The output unit is configured to provide an instant of contrast agent arrival in the field of view of the anatomy of interest as a function of the instant along time with the maximum change of contrast.

According to an example, for providing the instant of contrast agent arrival, the processing unit is configured to provide the instant along time with the change of the contrast as an indicator of a starting of contrast injection of the anatomy of interest.

According to an example, the processing unit is configured to measure the contrast as a contrast of a location on the catheter with respect to a surrounding of the catheter.

According to an example, the processing unit is configured to register the at least one location for measuring contrast with the catheter such that when the catheter moves in relation with the image frame of reference, also the at least one location for measuring contrast moves in the image in relation to the image frame of reference.

According to the present invention, also a system for interventional medical X-ray imaging is provided. The system comprises an X-ray image acquisition device, an image processing device, and a catheter for delivery of contrast agent. The catheter is configured for insertion in an anatomy of interest and a delivery of contrast agent in the anatomy of interest. The X-ray image acquisition device is configured to provide a temporal sequence of X-ray image data comprising a plurality of frames with a field of view of an anatomy of interest and the catheter inserted for delivery of contrast agent. The image processing device is provided as an image processing device according to one of the above-mentioned examples.

According to an aspect, the contrast arrival is detected directly over the catheter footprint. This allows a robust detection, since the catheter has a very identifiable silhouette, such as a fix width and a simple shape. This allows an early reaction, since contrast agent may be detected even prior to its arrival in the vessels. The injection catheter is detected, which catheter may be weakly contrasted before injection, but still detectable due to well identifiable characteristics. The contrast change (e.g. average contrast change, maximum contrast change, or substantial contrast change) over the catheter footprint is then monitored. The contrast at a given instant can be estimated as an absorption difference between the exterior and the interior of the catheter at that point, i.e. location. This assumes that the X-ray images are considered in the so-called "linear domain", that is after the application of a logarithm look-up-table that makes these images absorption images where each pixel value is linearly linked to the sum of all the absorbing material layers encountered along the rays impacting this pixel. In an example, for each frame of a sequence, a catheter is extracted and for each position alongside the catheter, the contrast profiles are extracted. The measured contrasts may be integrated over the length of the catheter. The two successive frames that present the maximal change in the contrast integral are then selected. The injected frame is then provided as an output, i.e. the second frame of the previous selection is provided. Hence, the catheter is used as a contrast injection marker.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 1 shows basic steps of an example of a method for detection of contrast agent arrival in X-ray imaging;

FIG. 2 shows steps of a another example of the method for detection of contrast agent arrival;

FIG. 4 shows an illustration of an anatomy of interest with an inserted catheter and a marked location of a contrast curve selection for measurement of contrast, wherein

FIG. 9 shows the content of FIG. 4 as photographic X-ray images, wherein FIG. 9A relates to FIG. 4A, and FIG. 9B relates to FIG. 4B; and FIG. 10 shows the image content of FIG. 6 as a photographic X-ray image representation.

DETAILED DESCRIPTION OF EMBODIMENTS

Figure 3:
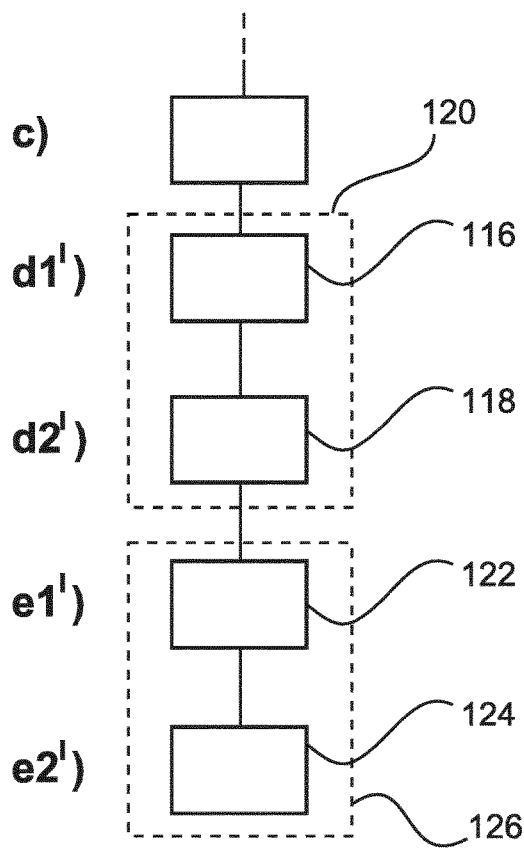
FIG. 3 shows steps of a further example of the method for detection of contrast agent arrival.

FIG. 1 shows a method 100 for detection of contrast agent arrival in X-ray imaging. In a first step 102, a temporal sequence of X-ray image data is provided. The sequence comprises a plurality of frames with a field of view of an anatomy of interest and an inserted catheter for delivery of contrast agent. In the field of view, contrast agent is injected with the catheter during the temporal sequence. In a second step 104, at least one location for measuring contrast is determined in each of the frames. The at least one location for measuring contrast pertains to a portion of the catheter along a length of the catheter in the field of view in the image data.

In a third step 106, contrast is measured at the at least one location for each of the frames at least in the image part pertaining to the portion of the catheter.

In a fourth step 108, a change of the measured contrast is determined along time at the at least one location pertaining to the portion of the catheter.

In a fifth step 110, the instant along time with the change of the contrast is provided as an indicator of a starting of contrast injection of the anatomy of interest.

The first step 102 is also referred to as step a), the second step 104 as step b), the third step 106 as step c), the fourth step 108 as step d), and the fifth step 110 as step e).

The contrast change (or the change of the measured contrast) may be a maximum change of the measured contrast, an average change of the measured contrast, a substantial change of the measured contrast, or any other changes that can indicate the increased presence of contrast agent.

According to an example, the change of the contrast comprises a maximum change of the measured contrast.

In an example, in the fourth step 108, i.e. in step d), a maximum change of the measured contrast along time is determined at the at least one location pertaining to the portion of the catheter. In the fifth step 110, i.e. in step e), an instant of contrast agent arrival is provided in the field of view of the anatomy of interest as a function of the instant along time with the maximum change of contrast.

The field of view shows the anatomy of interest as a region of interest. The anatomy of interest may relate to a part of a vessel structure of a patient, for example. The location for measuring contrast is thus forming a part of the region of interest. In other words, the location for measuring contrast is also forming a region of (particular) interest, but a smaller image area than the area of the field of view.

The contrast arrival is detected over the catheter footprint. Hence, the catheter is provided as a contrast injection marker.

In an example, the sequence of X-ray data is provided as fluoroscopy images. In another example, the sequence of X-ray data is provided as X-ray images.

In another example, the first position is close to a contrast agent release opening of the catheter, out of which opening contrast is injected into the vessel structure, but the first position is still on the catheter.

In an example, not further shown in detail, the contrast is measured as a contrast of a location on the catheter with respect to a surrounding of the catheter.

In a further example, the at least one location for measuring contrast is registered with the catheter such that when the catheter moves in relation with the image frame of reference, also the at least one location for measuring contrast moves in the image in relation to the image frame of reference. After the determination, the at least one location for measuring contrast is not allocated, or fixed, to certain image pixels, but allocated, fixed, to the image content in form of the catheter.

In an example, the at least one location for measuring contrast relates to a point (i.e. location) on the (projection of the) catheter.

In another example, the at least one location for measuring contrast relates to a point on the catheter in a predetermined distance to the tip of the catheter. In another example, the at least one location for measuring contrast relates to a point in a predetermined distance to a determined location on the catheter. For example, a distance of 2 cm from a catheter release opening can be a predetermined location.

In an example, in step c), for measuring the contrast, a first grey level is determined outside the catheter and a second grey level is determined inside the catheter. The first grey level is subtracted from the second grey level.

In another example, in step c) for measuring the contrast, contrast profiles are extracted. Preferably, the contrast profiles are extracted for a profile length that covers at least the width of the catheter and that is oriented in a profile direction transverse to a main catheter direction.

The contrast profile is also referred to as a contrast curve. In an example, the profile length covers the width of the catheter and the adjacent vessel area, for example extending to the vessel wall structure. In an example, the term "transverse" relates to perpendicular and the profile direction is arranged perpendicular to the main catheter direction. The term "perpendicular" relates to an angle of 90° that may comprise deviations of e.g. approximately +/−30°, such as +/−15° or +/−5°. The term "main catheter direction" relates to an orientation of a centre line of the catheter at the cross-section with the profile direction, respectively profile length.

The vessel area in the 2D projective image relates to the vessel volume, in which the catheter is arranged.

In a further example, not further shown in detail, in step c), the contrast profile comprises at least the inner part of the catheter and at least an adjacent part of an outer part of the catheter.

The term "inner" of the catheter relates to a section of the frame covered by the image data of the catheter. The term "outer" of the catheter relates to a section of the frame that is arranged in direct vicinity of the section that is covered by the image data of the catheter.

FIG. 2 shows a further example, in which for determining the change of the contrast along time, it is provided: Following step c), in a further step 112 the measured contrast for the at least one location is transferred on a temporal graph showing the contrast for the at least one location over the time of the sequence. This further step 112 is also referred to as step d1). For providing the indicator of a starting of contrast injection, it is provided: In a still further step 114, a part of the curve with the largest degree of inclination is determined. This further step 114 is also referred to as step e1).

In an example, the contrast is indicated by positive values, and the graph's reference system is having an upward (or vertically) oriented axis for the contrast. A large contrast has hence a higher point along the vertically oriented axis. An upcoming arrival of contrast agent, which results in a larger contrast, leads to a steeper degree of inclination of the curve of the graph. In other words, an angle of the function (curve) with a horizontal axis (for example indicating the time from left to right) would get larger. A rising curve thus indicates increasing contrast and a downward sloping curve indicates decreasing contrast. The degree of inclination (also referred to as inclination) thus represents the change of the contrast over time. The steeper the curve, the larger is the change. A contrast bolus, i.e. the arrival of injected contrast agent, would lead to a drastic change of the degree for inclination, i.e. the curve would suddenly rise in a steep manner. Slowly fading contrast would lead to a slowly or smoothly sloping curve.

FIG. 3 shows a further example, in which for determining the change of the contrast along time, it is provided: In a first sub-step 116, the change of contrast of successive frames is determined. In a second sub-step 118, two successive frames with maximal change of the contrast profiles are selected. The first sub-step 116 is also referred to as step d1'), and the second sub-step 118 is referred to as d2'). A dotted frame 120 indicates that the two sub-steps 116, 118 relate to the determining step d). For providing the indicator of a starting of contrast injection (i.e. instant along time), it is provided two sub-steps: In a further first sub-step 122, the one of the selected two frames with larger contrast values is determined as an injected frame. In a further second sub-step 124, the injected fame is provided as the indicator of the starting of contrast injection of the anatomy of interest. The first further sub-step 122 is referred to as e1'), and the further second sub-step 124 is referred to as step e2'). A further dotted frame 126 indicates that the two further sub-steps 122, 124 relate to step e).

The starting instant is also referred to as the beginning of the contrast injected frames, or a sub-sequence of frames. Also, the starting instant is referred to as contrast arrival.

In a further example, in step c), contrast profiles are extracted for a number of locations over a length of the catheter. Following step c), integrals of the contrast profiles are provided and in step d), the integrals are compared.

In a still further example, in step b), an extraction of the catheter is provided and in step b), for the extraction of the catheter in the frame, it is provided to extract at least one of the group of centreline of the catheter in the frame, outline of the catheter in the frame, and projected area of the catheter in the frame.

Figures 4A, 4B:
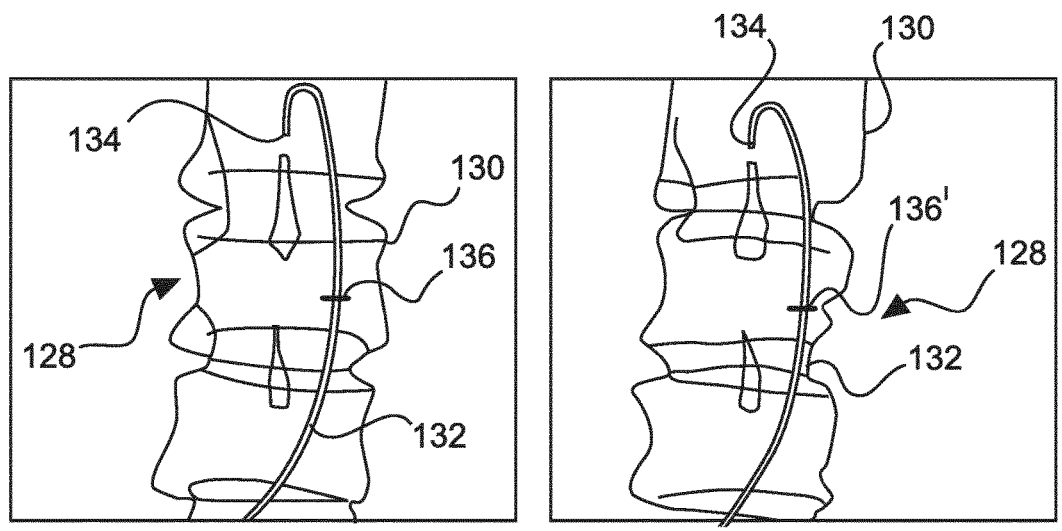
FIG. 4A shows the situation before contrast injection.
FIG. 4B shows the situation after contrast injection.

FIG. 4A shows an image 128 of an anatomy of interest. For example, the anatomy of interest is a region of interest of a patient, the region of interest comprising a vertebral structure 130. Further, a catheter 132 is shown, wherein the catheter may be inserted into a vessel structure for contrast agent injection. For example, the catheter 132 may have a catheter tip 134, for injecting the contrast agent into the vessel structure in order to visualize the vessel structure. An indicator 136 represents a determined location for measuring contrast in each of the frames, wherein FIG. 4A shows one of the frames of a temporal sequence of X-ray image data. The at least one location for measuring contrast pertains to a portion of the catheter in the field of view in the image data. FIG. 4B shows the image of FIG. 4A, with an X-ray image as a frame of a temporal sequence of X-ray image data, showing the vertebral structure 130, as well as the catheter 132 with the catheter tip 134. Still further, a further indicator 136' indicates the location for measuring contrast.

FIG. 4A shows the situation before injection and FIG. 4B shows the situation after injection of contrast agent. As can be seen, in the frame of the sequence of X-ray image data, an injection of contrast agent cannot be detected by looking at the image. However, the location for measuring contrast on the catheter to a very precise and detailed contrast determination at this particular location, since the contrast agent inside the catheter moves, i.e. develops or flows, forward to the direction of the catheter tip and can thus be detected according to the present invention.

Figure 5:
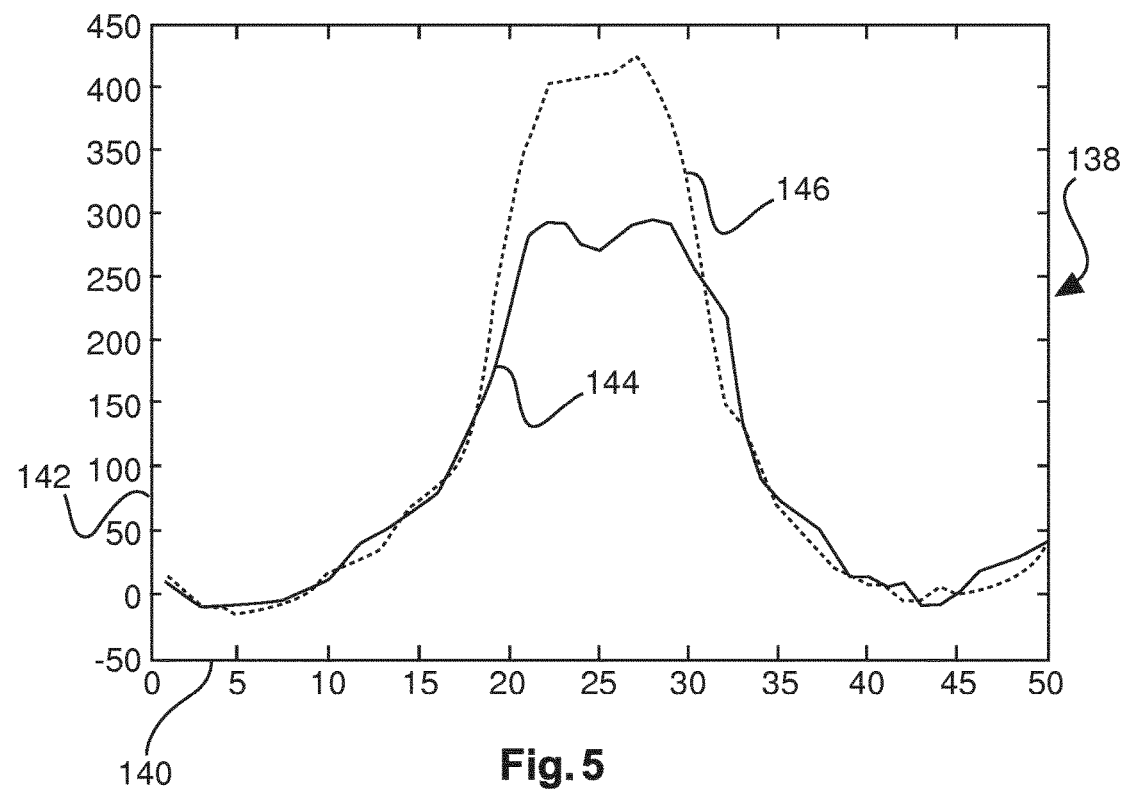
FIG. 5 shows contrast profiles perpendicular to a main catheter orientation at the location of FIG. 4A and 4B, wherein one contrast profile indicates the contrast before injection and another contrast profile indicates the contrast after injection.

In FIG. 5, a contrast profile graph 138 is shown. A first axis, the horizontal axis 140 indicates a geometric reference, i.e. a length of the indicators 136, 136'. A second, vertical axis 142 indicates the amount of contrast determined at the location for measuring contrast, which location pertains to a portion of the catheter. A first curve 144 indicates the contrast profile before injection, and a second curve 146 indicates the contrast profile after injection. In other words, the first curve 144 relates to the situation shown in FIG. 4A, and the second curve 146 relates to the situation in FIG. 4B. When comparing the two curves, a change of the contrast can be determined and thus, if all those profiles are considered along the time axis, the starting of contrast injection of the anatomy of interest is possible to be detected.

Figure 6:
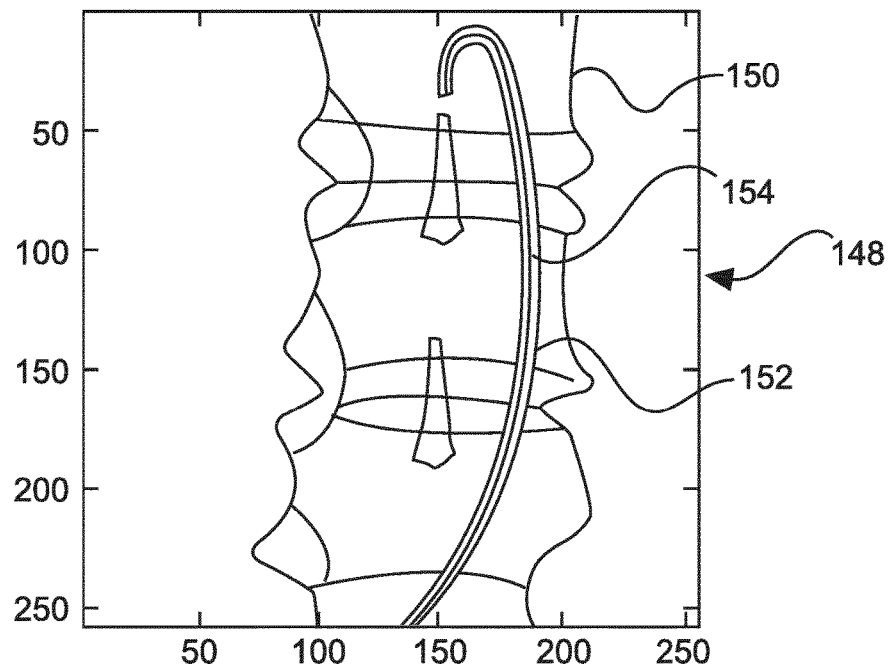
FIG. 6 shows an illustration of the anatomy of interest with an extracted catheter.

FIG. 6 shows an image 148 with an anatomy of interest, for example showing a vertebral structure 150. Further, a catheter 152 is shown. A centreline 154 indicates the extraction of the catheter for example used for the determination of the location for measuring contrast.

Figure 7:
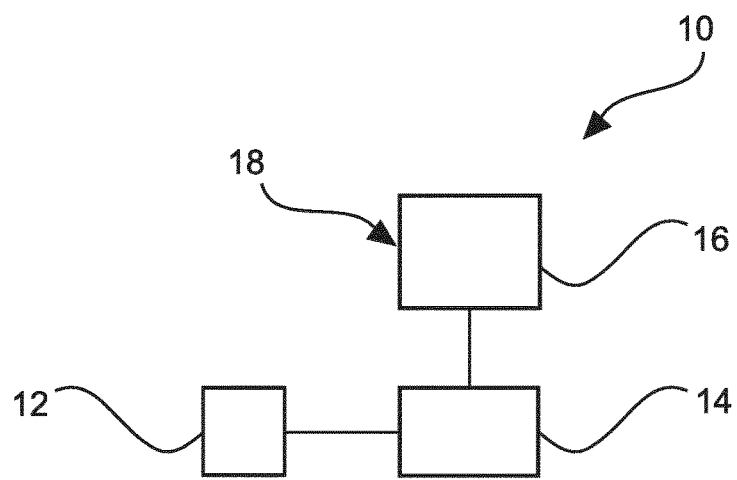
FIG. 7 shows a schematic setup of an image processing device for detection of contrast agent arrival in X-ray imaging.

FIG. 7 shows a schematic setup of an image processing device 10 for detection of contrast agent arrival in X-ray imaging. The image processing device 10 comprises an input unit 12, a processing unit 14 and an output unit 16. The input unit 12 is configured to provide a temporal sequence of X-ray image data comprising a plurality of frames with a field of view of an anatomy of interest and an inserted catheter for delivery of contrast agent. In the field of view, contrast agent is injected with the catheter during the temporal sequence. The processing unit 14 is configured to determine at least one location for measuring contrast in each of the frames. The at least one location for measuring contrast pertains to a portion of the catheter along a length of the catheter in the field of view in the image data. The processing unit 14 is further configured to measure contrast at the at least one location for each of the frames at least in the image part pertaining to the portion of the catheter. The processing unit 14 is further configured to determine a change of the measured contrast along time at the at least one location pertaining to the portion of the catheter. The output unit 16 is configured to provide the instant along time with the change of the contrast as an indicator of a starting of contrast injection of the anatomy of interest.

According to an example, the change of the contrast comprises a maximum change of the measured contrast.

In an example, the processing unit 14 is further configured to determine a maximum change of the measured contrast along time at the at least one location pertaining to the portion of the catheter. The output unit 16 is configured to provide the instant along time with the maximum change of the contrast as an indicator of a starting of contrast injection of the anatomy of interest.

In an example, the output unit is a display unit 18, shown as an option in FIG. 7. The display unit 18 is configured to display the injected frame as indicator of a beginning of a contrast injected sub-sequence of frames. The determined starting of contrast injection can be provided as information for further imaging procedures, such as, for example rotational image runs, or subtractions procedures, for example for digital subtraction angiography (DSA). The term "sub-sequence" relates to a part of an image sequence that also comprises non-injected frames as a further sub-sequence.

In an example, the processing unit 14 is configured to measure the contrast as a contrast of a location on the catheter with respect to a surrounding of the catheter.

In a further example, the processing unit 14 is configured to register the at least one location for measuring contrast with the catheter such that when the catheter moves in relation with the image frame of reference, also the at least one location for measuring contrast moves in the image in relation to the image frame of reference.

Figure 8:
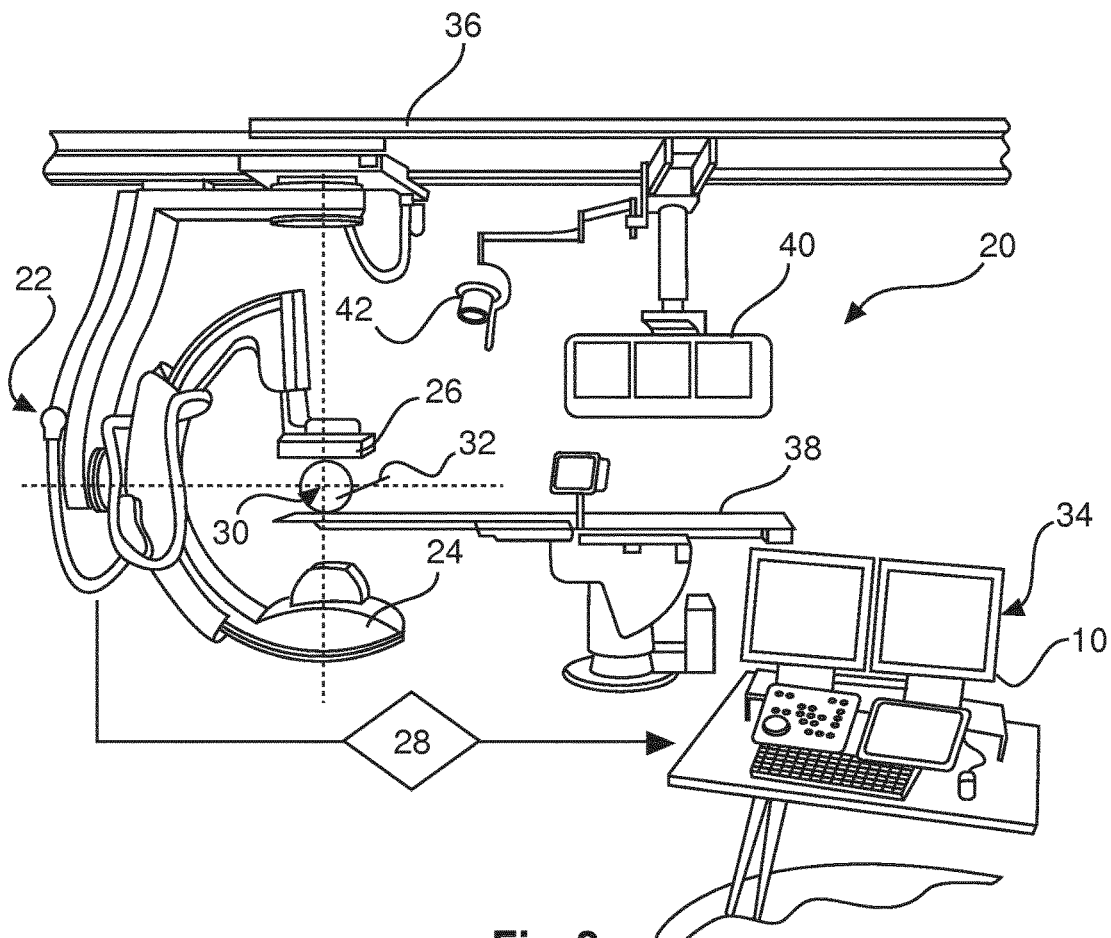
FIG. 8 shows a system for interventional medical X-ray imaging.

FIG. 8 shows a system 20 for interventional medical X-ray imaging. The system 20 comprises an X-ray image acquisition device 22, for example, with an X-ray source 24 and an X-ray detector 26. The X-ray image acquisition device 22 is configured to provide a temporal sequence 28 of X-ray image data comprising a plurality of frames with a field of view of an anatomy of interest 30.

The system further comprises a catheter 32 for delivery of contrast agent. The catheter 32 is configured for insertion in an anatomy of interest, as shown by the schematic representation in form of a spherical structure, with the reference number 30. The catheter is further configured to deliver a contrast agent in the anatomy of interest. The temporal sequence shows the X-ray image data with the catheter inserted for delivery of contrast agent.

The system 20 further comprises an image processing device 34 that is provided as an image processing device 10 according to the above-mentioned example, shown in FIG. 7 and described in the text above in further examples.

The X-ray image acquisition device 22 may be provided as a C-arm structure, as shown in FIG. 8, but may also be provided in different types of X-ray image acquisition systems. The C-arm system may be suspended from a ceiling structure 36 having a plurality of rails for adjusting the location of the X-ray image acquisition device in relation to a patient table 38. Further, display units 40 as well as lighting equipment 42 may be provided in a movable manner.

FIG. 9A shows a photographic illustration of the graphic representation in FIG. 4A. FIG. 9B shows a photographic illustration of the graphic representation in FIG. 4B. FIG. 10 shows a photographic illustration of the graphic representation in FIG. 6.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing device for detection of contrast agent arrival in X-ray imaging, comprising:
   are input;
   a processing circuit; and
   an output;
     wherein the input is configured to provide a temporal sequence of X-ray image data comprising a plurality of frames with a field of view of an anatomy of interest and an inserted catheter for delivery of contrast agent; wherein, in the field of view, contrast agent is injected with the inserted catheter during the temporal sequence of the X-ray image data;
   wherein the processing circuit is configured to determine at least one location for measuring contrast in each of the plurality of frames, wherein the at least one location for measuring contrast pertains to a portion of the inserted catheter along a length of the inserted catheter in the field of view in the X-ray image data; to measure contrast at the at least one location for each of the plurality of frames at least in a part of the X-ray image data pertaining to the portion of the inserted catheter; to determine a change of the measured contrast along time at the at least one location pertaining to the portion of the inserted catheter; and
     wherein the output is configured to provide an instant in time of arrival of a contrast agent in the field of view of the anatomy of interest as a function of the instant in time with the change of contrast.

2. The image processing device according to claim 1, wherein the change of the contrast comprises a maximum change of the measured contrast.

3. The image processing device according to claim 1, wherein, for providing the instant of time of the contrast agent arrival, the processing circuit is configured to provide the instant in time with the change of the contrast as an indicator of a starting of contrast injection of the anatomy of interest.

4. The image processing device according to claim 1, wherein the processing circuit is configured to measure the contrast as a contrast of a location on the inserted catheter with respect to a surrounding of the inserted catheter.

5. The image processing device according to claim 1, wherein the processing circuit is configured to register the at least one location for measuring contrast with the inserted catheter such that when the inserted catheter moves in relation with an image frame of reference, also the at least one location for measuring contrast moves in the image in relation to the image frame of reference.

6. A system for interventional medical X-ray imaging, comprising:
   an X-ray image acquisition device;
   an image processing device; and
   a catheter for delivery of contrast agent;
   wherein the catheter is configured for insertion in an anatomy of interest and a delivery of contrast agent in the anatomy of interest;
   wherein the X-ray image acquisition device is configured to provide a temporal sequence of X-ray image data comprising a plurality of frames with a field of view of an anatomy of interest and the catheter inserted for delivery of contrast agent; and
   wherein the image processing device is provided as an image processing device according to claim 1.

7. A method for detection of contrast agent arrival in X-ray imaging, the method comprising:
   a) providing a temporal sequence of X-ray image data comprising a plurality of frames with a field of view of an anatomy of interest and an inserted catheter for delivery of contrast agent; wherein, in the field of view, contrast agent is injected with the inserted catheter during the temporal sequence of the X-ray image data;
   b) determining at least one location for measuring contrast in each of the plurality of frames, wherein the at least one location for measuring contrast pertains to a portion of the catheter along a length of the inserted catheter in the field of view in the image data;

c) measuring contrast at the at least one location for each of the plurality of frames at least in a part of the X-ray image data pertaining to the portion of the inserted catheter;

d) determining a change of the measured contrast in time at the at least one location pertaining to the portion of the inserted catheter; and e) providing an instant of contrast agent arrival in the field of view of the anatomy of interest as a function of the instant in time with the change of contrast.

8. The method according to claim 7, wherein in step c), the contrast is measured as a contrast of a location on the inserted catheter with respect to a surrounding of the inserted catheter; and/or wherein in step c), for measuring the contrast, a first grey level is determined outside the inserted catheter and a second grey level is determined inside the inserted catheter, and the first grey level is subtracted by the second grey level.

9. The method according to claim 7, wherein the at least one location for measuring contrast is registered with the inserted catheter such that when the inserted catheter moves in relation with an image frame of reference, also the at least one location for measuring contrast moves in the image in relation to the image frame of reference.

10. The method according to claim 7, wherein in step c), for measuring the contrast, contrast profiles are extracted; and wherein the contrast profiles are extracted for a profile length that covers at least the width of the catheter and that is oriented in a profile direction transverse to a main direction of the inserted catheter.

11. The method according to claim 10, wherein in step c), the contrast, profiles comprise at least the inner part of the catheter and at least an adjacent part of an outer part of the catheter.

12. The method according to claim 7, wherein in step c), contrast profiles are extracted for a number of locations over a length of the catheter; and wherein following step c), integrals of the contrast profiles are provided; and wherein in step d), the integrals are compared.

13. The method according to claim 7, wherein in step b), the catheter is extracted; and wherein for the extraction of the catheter in the frame it is provided to extract at least one of:

centreline of the catheter in the frame, outline of the catheter in the frame, and projected area of the catheter in the frame.

14. A non-transitory computer-readable storage medium that stores machine executable instructions, which, when being executed by a processing circuit, is adapted to perform the method of claim 7 for detection of contrast agent arrival in X-ray imaging.

* * * * *